(12) United States Patent
Bekx et al.

(10) Patent No.: US 8,455,684 B2
(45) Date of Patent: Jun. 4, 2013

(54) METHOD FOR CONVERTING AROMATIC ALDEHYDES TO AROMATIC ACYL HALIDES

(75) Inventors: Hendrikus Bekx, Herpen (NL); Henk Knoester, Arnhem (NL)

(73) Assignee: Teijin Aramid B.V., Arnhem (NL)

( * ) Notice: Subject to any disclaimer, the term of this patent is extended or adjusted under 35 U.S.C. 154(b) by 0 days.

(21) Appl. No.: 13/256,316

(22) PCT Filed: Mar. 10, 2010

(86) PCT No.: PCT/EP2010/053022
§ 371 (c)(1),
(2), (4) Date: Sep. 13, 2011

(87) PCT Pub. No.: WO2010/105950
PCT Pub. Date: Sep. 23, 2010

(65) Prior Publication Data
US 2012/0004461 A1  Jan. 5, 2012

(30) Foreign Application Priority Data

Mar. 17, 2009  (EP) ..................................... 09155378

(51) Int. Cl.
*C07C 51/60* (2006.01)
(52) U.S. Cl.
USPC ........................................................ 562/863
(58) Field of Classification Search
CPC ....................................................... C07C 51/60
IPC ....................................................... C07C 51/60
See application file for complete search history.

(56) References Cited

U.S. PATENT DOCUMENTS

| 1,880,169 | A | * | 9/1932 | Bennett et al. ................ 562/859 |
| 2,791,608 | A | | 5/1957 | Golding |
| 3,274,242 | A | | 9/1966 | Etherington, Jr. et al. |
| 3,894,923 | A | | 7/1975 | Grégoire |
| 3,950,414 | A | | 4/1976 | Koch |
| 5,872,291 | A | | 2/1999 | Koshikawa et al. |
| 6,187,952 | B1 | | 2/2001 | Pfirmann et al. |

FOREIGN PATENT DOCUMENTS

BE  647037  10/1964

OTHER PUBLICATIONS

Jun. 1, 2010 International Search Report issued in International Application No. PCT/EP2010/053022.
Jun. 1, 2010 Written Opinion issued in International Application No. PCT/EP2010/053022.
Solly, R. et al., "Thermochemistry of the reaction of benzaldehyde with iodine. The enthalpy of formation of benzaldehyde and benzoyl iodide," Journal of Chemical Thermodynamics, vol. 3, No. 2, 1971, pp. 203-209.
Chambers, R. et al., "Elemental Fluorine. Part 21. Direct Fluorination of Benzaldehyde Derivatives," Organic Process Research & Development, vol. 12, No. 2, 2008, pp. 339-344.

* cited by examiner

*Primary Examiner* — Paul A Zucker
(74) *Attorney, Agent, or Firm* — Oliff & Berridge, PLC

(57) ABSTRACT

A method for converting an aromatic aldehyde or a mixture of aromatic aldehydes to a reaction product in a reaction medium that is free from xylene. The reaction product may be an aromatic acyl halide or a mixture of aromatic acyl halides. The method includes bringing the aromatic aldehyde or mixture of aromatic aldehydes in contact with a halogen to obtain the reaction product.

10 Claims, No Drawings

METHOD FOR CONVERTING AROMATIC ALDEHYDES TO AROMATIC ACYL HALIDES

BACKGROUND

This disclosure pertains to a method for converting an aromatic aldehyde or a mixture of aromatic aldehydes to an aromatic acyl halide or a mixture of aromatic acyl halides.

Methods for converting an aromatic aldehyde to aromatic acyl halide are known in the art. For instance, in U.S. Pat. No. 3,274,242 the preparation of aromatic acyl chlorides by vapor phase chlorination of aromatic aldehydes is described at temperatures of 225° C. or higher. This method has the disadvantage that high temperatures must be used, which makes the process expensive, and for terephthaldehyde (TPAL) only a low yield was obtained.

In BE 647037, a method is disclosed wherein neat chloro-substituted aromatic aldehydes were brought in contact with chlorine gas at moderate temperatures. This method only worked for chloro-substituted aromatic aldehydes and rendered yields around 80%.

In U.S. Pat. No. 3,894,923, the conversion to benzoyl chloride is described by chlorinating neat liquid benzaldehyde using UV light and/or peroxides as catalyst. This method was only claimed for the conversion of benzaldehyde to benzoyl chloride.

In U.S. Pat. No. 2,791,608, phthaloyl chloride is prepared from oxidation of xylene in the presence of an oxidation catalyst followed by chlorination of the oxidation product. Inert solvents may be used, including aromatic dicarbocylic acid chlorides. The reaction mixture may contain toluic acids, phthalic acids, methyl and carboxy benzaldehydes, and methylbenzyl toluates. This preparation method has several disadvantages. Part of the product will be ring chlorinated due to the presence of oxidation catalysts. Accurate control of the equimolarity of methyl and acid groups in the mixture is essential. Any unbalance in the presence of these functional groups will lead to formation of significant amounts of side products that are difficult to remove from the reaction mixture. Furthermore, it is also required to remove water that is formed during oxidation to avoid formation of side products during the chlorination step. Finally, the complexity of the method, comprising oxidation, chlorination and fusion steps, is disadvantageous as well.

A method for making terephthaloyldichloride (TDC) from an aromatic aldehyde is disclosed in U.S. Pat. No. 3,950,414, wherein the preparation of aromatic diacyl chlorides is described by chlorination of aromatic dialdehydes in an inert solvent, such as carbon tetrachloride or another fully halogenated aliphatic hydrocarbon.

TPAL is converted by reaction with chlorine in carbon tetrachloride (CTC) as a solvent in high yields at moderate temperatures. According to this method TPAL can be moderately dissolved in CTC at temperatures of about 35° C., and can be chlorinated with high conversion and high selectivity by subjecting the solution or slurry to chlorine gas. The reaction rate, conversion, and selectivity of the reaction are not influenced by the presence of light. The reaction goes perfectly well in complete darkness.

However, due to more stringent environmental requirements, the use of carbon tetrachloride and other halogenated aliphatic hydrocarbons is no longer acceptable, and industrial processes using this solvent no longer can count on governmental license due to the solvent's detrimental effects on the ozone layer. Therefore a process having similar high yields and selectivity, whereas the reaction conditions in teams of reaction time and reaction temperature are equally favorable, as processes using aliphatic hydrocarbon solvents are desired.

According to the present disclosure it has now been found that TPAL can be converted to TDC under similar reaction conditions giving similar yields and selectivity, without using toxic halogenated solvents. It was also found that the present method could advantageously be used for other aromatic aldehydes as well.

SUMMARY

The present disclosure relates to a method for converting an aromatic aldehyde or a mixture of aromatic aldehydes to a reaction product which is an aromatic acyl halide or a mixture of aromatic acyl halides in a reaction medium which is free from xylene, comprising bringing the aromatic aldehyde or mixture of aromatic aldehydes in contact with a halogen to obtain the reaction product, wherein the reaction medium optionally comprises a co-solvent selected from the group consisting of any aromatic acyl halide and mixtures thereof.

DETAILED DESCRIPTION

The reaction for TPAL and chlorine is given by the reaction equation

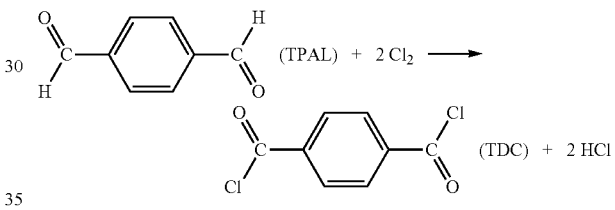

In embodiments, the method may use the reaction product as solvent, optionally in the presence of a co-solvent.

Throughout the below description, the terms "compound", "reaction product", "aromatic aldehyde", and "aromatic acyl halide" have the meaning "compound or compounds", "reaction product or reaction products", "aromatic aldehyde or mixture of aromatic aldehydes", and "aromatic acyl halide or mixture of aromatic acyl halides", respectively.

In embodiments, the same compound as the reaction product may be selected as co-solvent. This makes isolation of the reaction product very simple and makes it possible that no other solvents have to be isolated and regenerated. In embodiments, a compound other than the reaction product is selected as co-solvent to lower the reaction temperature. In embodiments, a compound that has a different crystallization behavior than the reaction product may be used as co-solvent in order to facilitate isolation of the reaction product. It is also possible to dispense from any co-solvent and to start with neat aromatic aldehyde. The reaction product thereby formed acts as solvent. In the reaction medium of aromatic aldehyde and the optional co-solvent, the amount of co-solvent is 0-95% by weight, such as 40-90% by weight. The co-solvent may exclusively or virtually exclusively (i.e. about 98-100%) contain the reaction product, or a mixture of reaction product and another aromatic acyl halide that can easily be separated by crystallization. If a co-solvent is used, the co-solvent may be added to the mixture prior to the reaction or during the reaction. For the conversion of TPAL with chlorine, TDC is the reaction product and TDC and/or IDC may be present as co-solvents. A suitable amount of TDC (as co-solvent) in the mixture is about 90% by weight with regard to TPAL. For the conversion of other aromatic aldehydes, similar amounts of co-solvent may be used. Although the same may be used as the co-solvent and as the product that is obtained by converting the aromatic aldehyde, other aromatic acyl halides, or mixtures of aromatic acyl halides, may be used as the co-solvent.

Methods according to embodiments no longer uses xylenes, such as para-, meta- or ortho-xylene or other alkylarenes, or heavy metal catalysts.

It may be advantageous to enhance the reaction rate by irradiating the reaction medium with actinic light. Irradiation may be done during the whole reaction period or during part of the period that the aromatic aldehyde is brought in contact with the halogen.

The term "co-solvent" relates to the aromatic acyl halide that is present in the reaction medium before the reaction has started and/or that is added during the reaction, and which is not a reactant of the reaction. At the end of the reaction, the mixture contains reaction product, which is the solvent, and optionally co-solvent. The reaction product may be the same or a different compound as the co-solvent, and as such acts as a solvent for the aromatic aldehyde reactant. However, the reaction product, whether or not the same compound as the co-solvent, is not included in the definition of the term "co-solvent".

The term "aromatic acyl halide" stands for the reaction product that is obtained from the aromatic aldehyde. The term "any aromatic acyl halide" stands for the reaction product or any other aromatic acyl halide. Isophthaloyldichloride (IDC) and TDC are the most common aromatic acyl halides that can be made as a reaction product or used as a co-solvent, but their corresponding bromides and iodides, and their substituted analogous compounds, including annealed compounds such as naphthaloyldichloride may also be used.

Isophthaldehyde (IPAL) or TPAL may be easily dissolved in IDC or TDC, or in a mixture thereof, and may be chlorinated at temperatures above the melting point of IDC (42-43° C.) or TDC (79-81° C.) by subjecting the mixture to chlorine gas. If mixtures of solvents and co-solvents are used, the mixtures may be eutectic mixtures. A eutectic mixture, in the sense of this disclosure, is a mixture at such proportions that the melting point is as low as possible, such as not more than 10° C., for example not more than 5° C. higher than the minimum melting point.

In general, a co-solvent may be selected wherein the aromatic aldehyde dissolves at low temperatures, such as below 90° C., for example at room temperature. The co-solvent may be any aromatic acyl chloride, such as TDC, IDC, benzoyl chloride, and the like, and mixtures thereof.

At moderate temperatures (90° C.) the reaction rate is low and a limited conversion is obtained (30-50%) at commercially acceptable reaction times, although at high selectivity. Side products other than the intermediate product 3- or 4-formylbenzoylchloride (3-FBC or 4-FBC) could not be detected. Irradiation with actinic light was found to enhance the reaction rate considerably, rendering TPAL conversions of more than 90%. It was further found that halogen light gave the best results in terms of suppressing formation of Cl-TDC (chloro-terephthaloyldichloride) as side product.

IPAL may easily be converted to IDC in TDC as a co-solvent. The mixture at the end of the reaction then contains IDC as the reaction product and TDC as the co-solvent. IDC may be easily separated from TDC by crystallization. In embodiments, IPAL may be converted to IDC in IDC as a co-solvent, not requiring any further crystallization. If the lowest possible conversion temperatures are important, a eutectic mixture of IDC and TDC may be used, and the reaction product may be separated from TDC by crystallization.

In embodiments, TDC may be made by dissolving TPAL in a eutectic mixture of IDC and TDC, adding chlorine, and, after finishing the conversion of TPAL to TDC, separating TDC from the co-solvent IDC by crystallization.

Suitable amounts of aromatic aldehyde with regard to the amount of reaction medium at the start of the reaction may be 5 to 100 wt %, such as 10 to 60 wt %, based on the reaction medium weight. Amounts lower than 10 wt % are economically unattractive and amounts higher than 60 wt % require high reaction temperatures.

Embodiments for making TDC from TPAL have major advantages over the known route, because they may be a simple one-step process and the chlorine demand and hydrochloric acid formation are 33% less than the method of U.S. Pat. No. 2,791,608.

EXAMPLES

The disclosure is illustrated by the following non-limiting examples:

General

A one (1) liter Schott bottle was used as reaction vessel, equipped with a temperature sensor and a gas inlet sparger. Mixing was achieved with a magnetic stirrer.

The reactor, fixed to a metal frame, was hung in a pan filled with hot water, which was used to establish the desired reaction temperature.

Chlorine was fed to the reactor vessel from a small sized $Cl_2$ cylinder. The gas flow was controlled by a beforehand calibrated mass flow controller and led through a filter to remove moisture. Before and after $Cl_2$ dosing, the reactor content was purged with nitrogen gas.

The reaction mixture was subjected to a mixture of $N_2$ (g) and $Cl_2$ (g).

The off-gas from the experiments is a mixture of $N_2$, $Cl_2$, and HCl, which was led through an off-gas 'street' of three absorption bottles in series filled with water/caustic soda (bottle 1), water (bottle 2) and water/caustic soda (bottle 3).

The off-gas was led over the content of bottles 1 and 2 and led through the content of bottle 3. $Cl_2$ will preferably absorb in caustic soda and HCl in both caustic soda and water.

By measuring the weights of the absorption bottles before and after the experiment, one obtains an indication of the total amounts of $Cl_2$ and HCl in the off-gas. A distinction between HCl and $Cl_2$ can be made when bottle 1 is filled with water.

For the irradiation experiments, either a 20 W or 50 W halogen light source was used, or a 150 W high-pressure mercury light source (emitting predominantly in the UV part of the light spectrum) was used.

IDC, IPAL, and TPAL were purchased from Sigma-Aldrich (purity>99%); $Cl_2$ was obtained from a small sized cylinder (12.5 Kg) with purity 2.8 (equivalent to>99.8 vol %).

TDC was obtained from the TDC plant of Teijin Aramid, Delfzijl, the Netherlands.

Example 1

14.9 g of TPAL (111 mmole) were dissolved in 600 mL of TDC. About two times the stoichiometrically required amount of chlorine was bubbled through the mixture while the mixture was kept at a constant temperature of 90° C. During the first 53 minutes, 346 mmole of $Cl_2$ were added to the mixture (at a constant rate of 6.5 mmole/min) followed by an extra 66 mmole of $Cl_2$ in 2 hours and 17 minutes (0.5 mmole/min).

Gas chromatographic analysis of a sample of the final reaction mixture showed 50% conversion of TPAL while obtaining a significant amount of 4-formylbenzoylchloride (4-FBC).

Example 2

Example 1 was continued while irradiating the reaction mixture with a high-pressure mercury UV light source (150 W), positioned outside the reactor.

During 56 minutes 362 mmole of $Cl_2$ were dosed (at a constant rate of 6.5 mmole/min) followed by another 66.5 mmole of $Cl_2$ in 2 hours and 18 minutes (0.5 mmole/min).

TPAL was almost fully converted into TDC while a small amount of ring chlorinated TDC was formed as well.

Example 3

12.6 g of TPAL (94 mmole) were dissolved in 560 mL of TDC. About two times the stoichiometrically required amount of chlorine was bubbled through the mixture at a constant temperature of 90° C. The mixture was irradiated by a 50 W halogen light source. During the first 59 minutes, 382 mmole of $Cl_2$ were added to the mixture (at a constant rate of 6,5 mmole/min) followed by an extra 71 mmole of $Cl_2$ in 2 hours and 28 minutes (0.5 mmole/min). Gas chromatographic analysis of a sample of the final reaction mixture shows almost full conversion of TPAL while obtaining a much better selectivity as compared to Example 2.

Example 4

10 g of TPAL and 10 g of IPAL (both 74.5 mmole) were dissolved in 500 mL of TDC. The mixture was irradiated by a 20 W halogen light source and kept at 90° C. during the experiment. During the first 50 minutes, 323.5 mmole of $Cl_2$ were added to the mixture (at a constant rate of 6.5 mmole/min) followed by an extra 79.5 mmole of $Cl_2$ in 2 hours and 45 minutes (0.5 mmole/min).

TPAL and IPAL were fully and high selectively converted into TDC and IDC respectively.

Example 5

10 g of TPAL and 10 g of IPAL (both 74.5 mmole) were dissolved in a 500 mL of TDC/IDC mixture with a TDC content of 30 mass %. The mixture was irradiated by a 20 W halogen light source and kept at 50-55° C. during the experiment.

During the first 45 minutes, 291 mmole of $Cl_2$ were added to the mixture (at a constant rate of 6.5 mmole/min) followed by an extra 75 mmole of $Cl_2$ in 2 hours and 35 minutes (0.5 mmole/min).

TPAL and IPAL were fully and high selectively converted into TDC and IDC respectively. Already after the first 45 minutes, TPAL and IPAL were vanished completely, though peaks could be identified representing the half products 4-FBC and 3-FBC.

Example 6

10.29 g of TPAL (76.7 mmole) and 5.42 g of IPAL (40.4 mmole) were dissolved in a 500 mL of TDC/IDC mixture with a TDC content of 30 mass %. The mixture was not irradiated and kept at 45-50° C. during the experiment. During the first 45 minutes, 291 mmole of $Cl_2$ were added to the mixture (at a constant rate of 6.5 mmole/min) followed by an extra 128 mmole of $Cl_2$ in 3 hours and 45 minutes (0.56 mmole/min).

The final product showed a full and highly selective conversion of TPAL and IPAL in TDC and IDC respectively.

Example 7

9.9 g of TPAL (73.8 mmole) and 3.32 g of IPAL (both 24.8 mmole) were dissolved in a 500 mL of TDC/IDC mixture with a TDC content of 30 mass %.

The mixture was irradiated by a 20 W halogen light source and kept at 43° C. during the experiment. During 30 minutes, 194 mmole of $Cl_2$ were added to the mixture (at a constant rate of 6.5 mmole/min).

The final product showed a full and highly selective conversion of TPAL and IPAL in TDC and IDC respectively.

Example 8

189 g of TPAL (1409 mmole) were dissolved in a 355 mL of TDC/IDC mixture with a TDC content of 30 mass %. The mixture was irradiated by a 20 W halogen light source and kept at 75° C. during the experiment. During 3 hours and 6 minutes, 1522 mmole of $Cl_2$ were added to the mixture (at a constant rate of 8.2 mmole/min), TPAL was only partially converted into 4-FBC and TDC.

Example 9

10.32 g of TPAL (76.9 mmole) were dissolved in 500 mL of benzoylchloride.

The mixture was irradiated by a 20 W halogen light source and kept at room temperature (22° C.) during the experiment. During 30 minutes, 194 mmole of $Cl_2$ were added to the mixture (at a constant rate of 6.5 mmole/min).

The final product showed a full and highly selective conversion of TPAL in TDC.

Example 10

34.4 g of TPAL (257 mmole) and 46.6 g of IPAL (348 mmole) were molten.

The viscous mixture (without co-solvent) was irradiated by a 20 W halogen light source and kept at 90° C. during the experiment. During 4 hours, 1440 mmole of $Cl_2$ were added to the mixture (at a constant rate of 6 mmole/min).

Due to the high viscosity the conversion was only 43% and the selectivity was 44%.

The invention claimed is:

1. A method for converting an aromatic dialdehyde or a mixture of aromatic dialdehydes to a reaction product without the use of xylene, comprising:
reacting the aromatic dialdehyde or the mixture of aromatic dialdehydes with a halogen in a reaction medium that comprises a solvent, the solvent comprising an aromatic acyl halide or a mixture of aromatic acyl halides, wherein the reaction product comprises an aromatic diacyl halide for a mixture of aromatic diacyl halides.

2. The method according to claim 1, wherein the solvent comprises 98-100% by weight of the aromatic acyl halide or the mixture of aromatic acyl halides.

3. The method according to claim 1, further comprising irradiating the reaction medium with actinic light for at least part of the reaction.

4. The method according to claim 1, wherein the aromatic dialdehyde is terephthaldehyde, the solvent is terephthaloyldichloride, and the halogen is chlorine.

5. The method according to claim 1, wherein the aromatic dialdehyde is isophthaldehyde, the solvent is isophthaloyldichloride, and the halogen is chlorine.

6. The method according to claim 1, wherein
the aromatic dialdehyde is terephthaldehyde,
the solvent is a mixture of isophthaloyldichloride and terephthaloyldichloride, and
the halogen is chlorine,
wherein
the reaction product comprises terephthaloyldichloride, and,
after finishing the conversion of terephthaldehyde to terephthaloyldichloride, terephthaloyldichloride is separated from the solvent by crystallization.

7. The method according to claim 6, wherein the mixture of isophthaloyldichloride and terephthaloyldichloride is a eutectic mixture.

8. The method according to claim 1, wherein the halogen is chlorine.

9. The method according to claim 1, wherein the reaction medium comprises the aromatic dialdehyde in an amount of from 10 to 60 wt %.

10. The method according to claim 1, wherein the reaction medium comprises the solvent in an amount of from 40 to 90 wt %.

* * * * *